United States Patent
Pivonka

(10) Patent No.: US 7,470,395 B2
(45) Date of Patent: Dec. 30, 2008

(54) MOBILE FLAME STERILIZER

(75) Inventor: Ralph M. Pivonka, Lacrosse, KS (US)

(73) Assignee: Flame Engineering, Inc., Lacrosse, KS (US)

( * ) Notice: Subject to any disclaimer, the term of this patent is extended or adjusted under 35 U.S.C. 154(b) by 640 days.

(21) Appl. No.: 10/687,854

(22) Filed: Oct. 17, 2003

(65) Prior Publication Data

US 2005/0084409 A1  Apr. 21, 2005

(51) Int. Cl.
*A61L 2/04* (2006.01)
*A01M 15/00* (2006.01)

(52) U.S. Cl. .............................. 422/1; 422/307; 47/1.44

(58) Field of Classification Search ................. 47/1.44; 747/1.44
See application file for complete search history.

(56) References Cited

U.S. PATENT DOCUMENTS

| 3,962,044 | A |   | 6/1976 | Mackenzie |   |
|---|---|---|---|---|---|
| 4,088,122 | A | * | 5/1978 | Miles | 126/271.2 R |
| 4,250,869 | A | * | 2/1981 | Doyle | 126/271.2 R |
| 4,420,901 | A | * | 12/1983 | Clarke | 47/1.44 |
| 4,805,927 | A | * | 2/1989 | Stephenson et al. | 172/47 |
| 5,030,086 | A | * | 7/1991 | Jones | 431/207 |
| 5,826,371 | A | * | 10/1998 | Benjamin | 47/1.44 |
| 6,014,835 | A |   | 1/2000 | Pivonka |   |
| 2003/0192485 | A1 | * | 10/2003 | Opfel | 119/526 |

FOREIGN PATENT DOCUMENTS

| GB | 1567505 | A | * | 5/1980 |
| JP | 06078658 | A | * | 3/1994 |
| JP | 1075704 | A | * | 3/1998 |

OTHER PUBLICATIONS 3-pages of an Executive Summary entitled LP-Gas for Weed and Nemalode Control in Agriculture dated Oct. 2001 by Wayne A. LePori—printed from the website shown at the bottom of the page from the Internet.

* cited by examiner

*Primary Examiner*—Elizabeth L McKane
(74) *Attorney, Agent, or Firm*—Sturm & Fix LLP

(57) ABSTRACT

A transportable flamer, mounted on a tractor or similar, may be used to sterilize poultry litter, soil, concrete, etc. The flamer disclosed comprises a hood to contain the heat, an external frame, and burners. A fuel tank may be carried on the flamer or on a tractor or trailer in front of, or behind the flamer. An additional embodiment provides for mounting the flamer on wheels, permitting the unit to be towed by a truck, four-wheeler, tractor, etc. The burners are adjustable as to angle, and fueling rate.

3 Claims, 8 Drawing Sheets

MOBILE FLAME STERILIZER

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates generally to a flamer. More particularly the present invention relates to a mobile flamer, attachable to the back of a tractor, for sterilizing poultry litter, soil, pavement, etc.

2. Background Art

Poultry litter may be sterilized by chemical means. As usual, the issue becomes that of chemical retention and the effect of the chemicals on the environment. Poultry litter may also be sterilized by flame heat, as disclosed by Mackenzie in U.S. Pat. No. 3,962,044. Because he discloses stationary equipment for litter sterilization, the method of Mackenzie '044 requires a significant investment in machinery to handle the litter for sterilization. Space for the machinery and appropriate shelter is also necessary.

A tractor drawn flamer was disclosed by Pivonka in U.S. Pat. No. 6,014,835 for the purpose of flame cultivation. Because of its open-flame design, the flamer of Pivonka '835 is not suitable for sterilization purposes. Because the use of the Pivonka '835 flamer for sterilization was not considered, there was no motivation to make the flamer enclosed for sterilization.

Handheld torches and flamers are available, again especially for weed control and ice melting. These flamers are not suitable for the large task of sterilizing large amounts of poultry litter or soil, etc. due to their small coverage and the weight that must be supported or drawn by the user.

There is therefore a need for a tractor drawn or tractor mounted flamer having adequate coverage to sterilize materials over a large area. There is an additional need for such a flamer having its flame enclosed to concentrate its heat; and to protect objects and people that might be harmed by the heat of flaming.

BRIEF SUMMARY OF THE INVENTION

An object of the present invention is to provide a flamer suitable for sterilizing material lying over a large area. Such materials include poultry litter, soil, and pavement. Other objects within this object include providing a flamer with an enclosed flame to concentrate the heat and to protect surroundings from the heat; and a flamer that is mobile so large areas may efficiently be sterilized with minimum manpower.

Tractors are ubiquitous in the agricultural industry. Because of tractors' versatility, implements are often made to mount to a tractor or be drawn behind a tractor. Heat has long been used for sterilization. So is it possible to utilize a tractor for transporting a flamer to provide heat for sterilization. Such a flamer is mounted on the tractor—preferably on a three-point hitch or quick coupler. An additional embodiment of the present invention is represented by a flamer on wheels or skids and drawn behind a vehicle as a trailer.

Other objects, advantages and novel features of the present invention will become apparent from the following detailed description of the invention when considered in conjunction with the accompanying drawings.

DETAILED DESCRIPTION OF THE INVENTION

Figure 1:
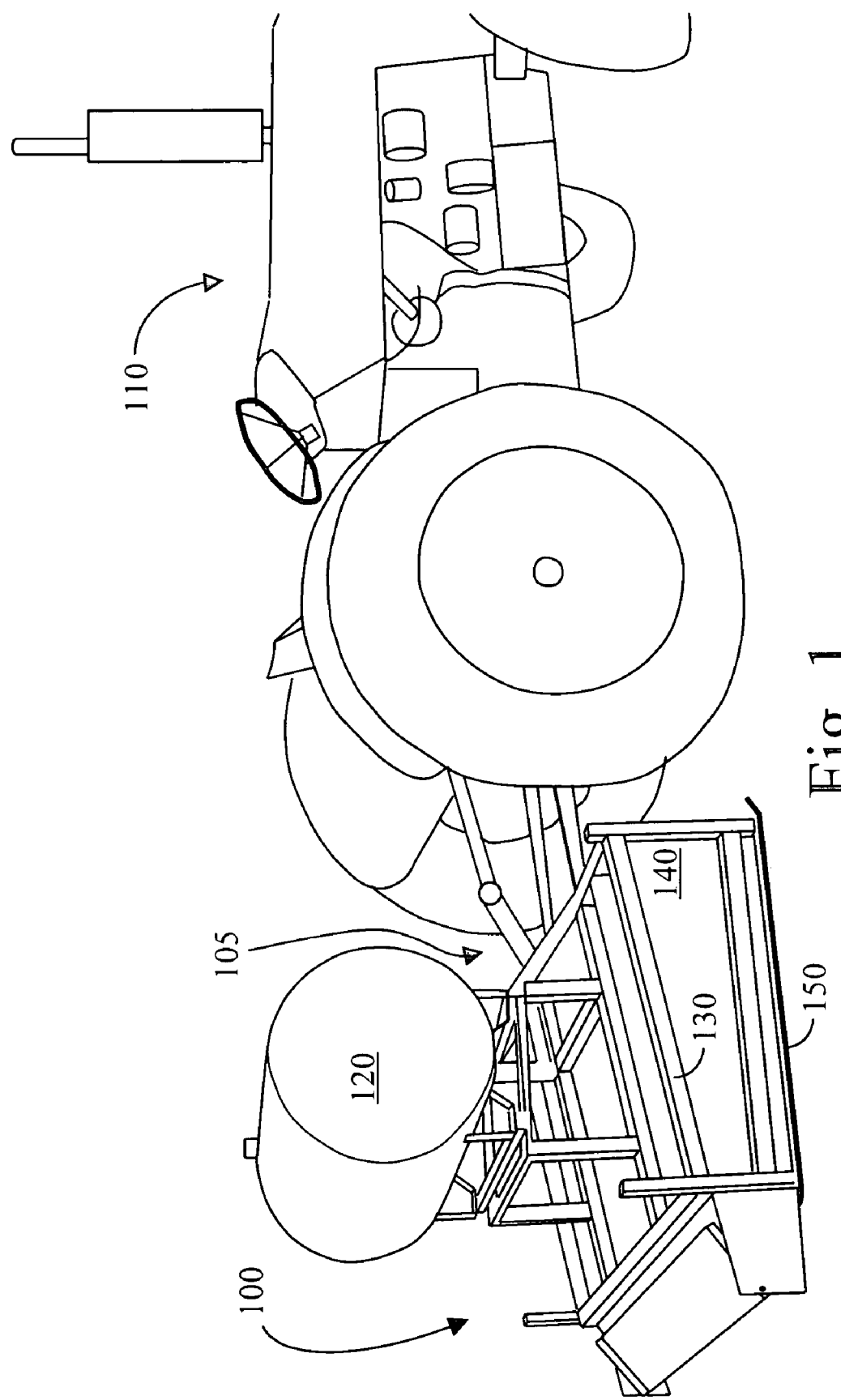
FIG. 1 is a perspective view of the tractor-mounted flamer with a fuel tank mounted thereon.
Figure 2:
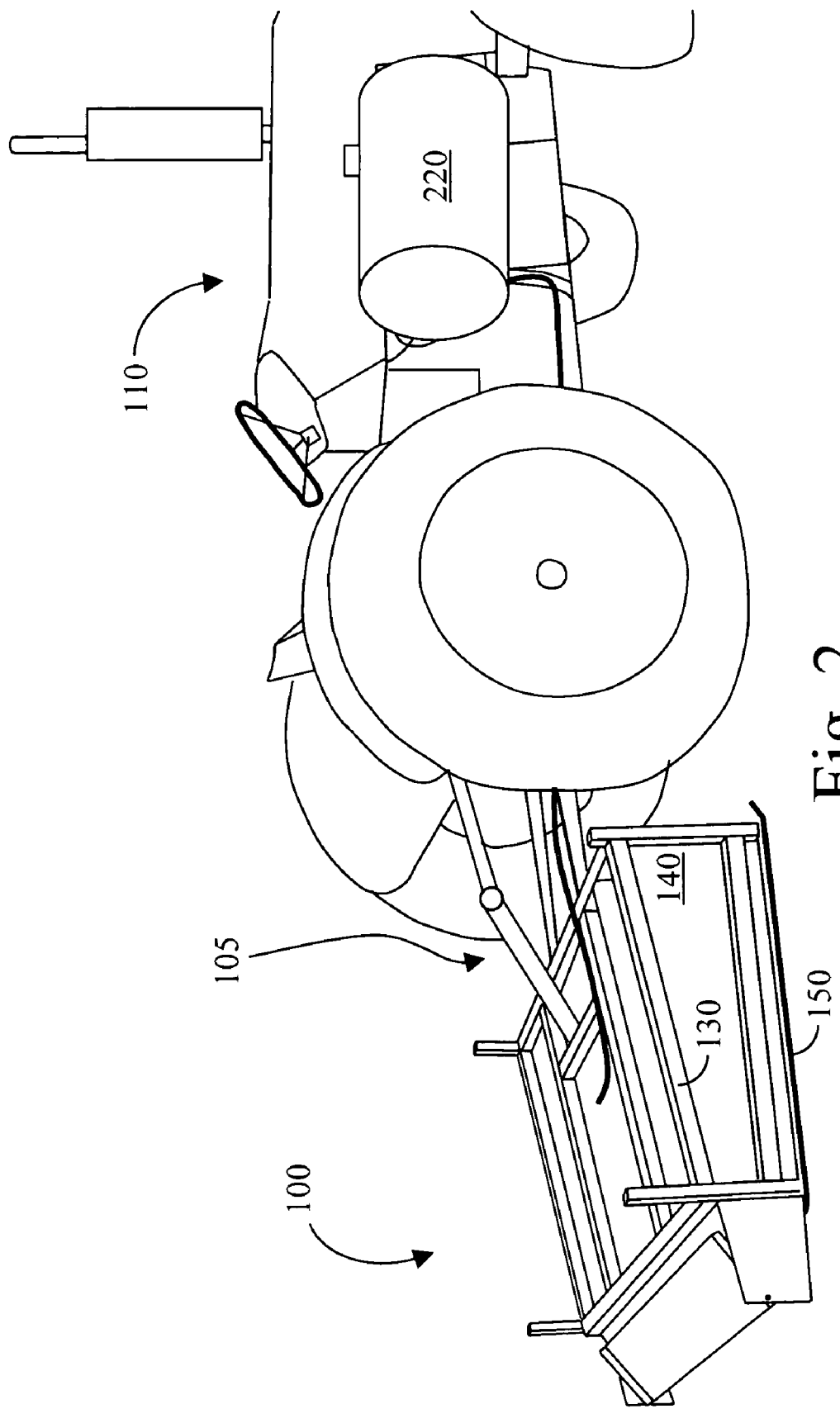
FIG. 2 is a perspective view of the tractor-mounted flamer with the fuel tank mounted on the side of the tractor.
Figure 3:
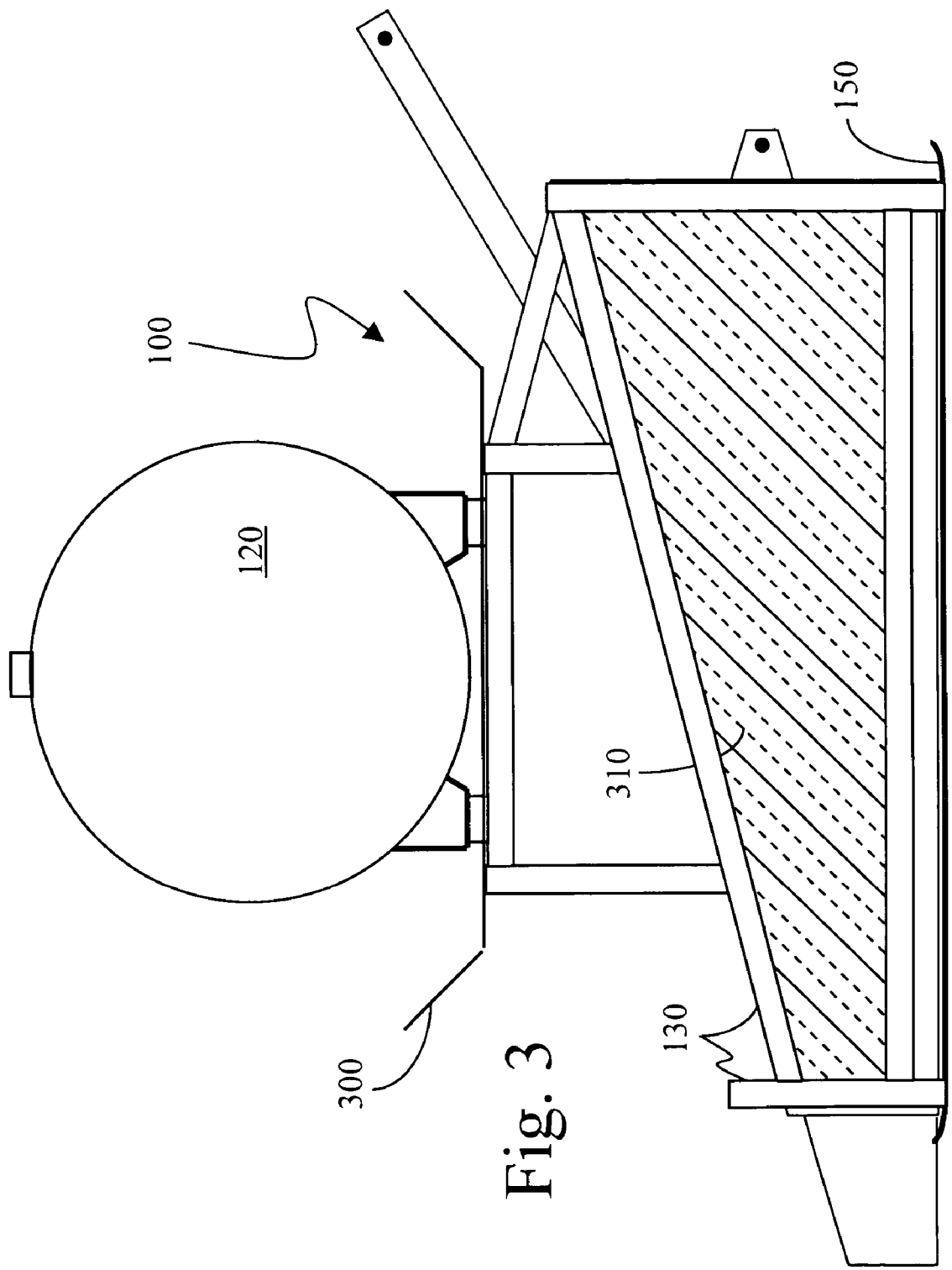
FIG. 3 is a side elevation view of the tractor-mounted flamer.
Figure 4:
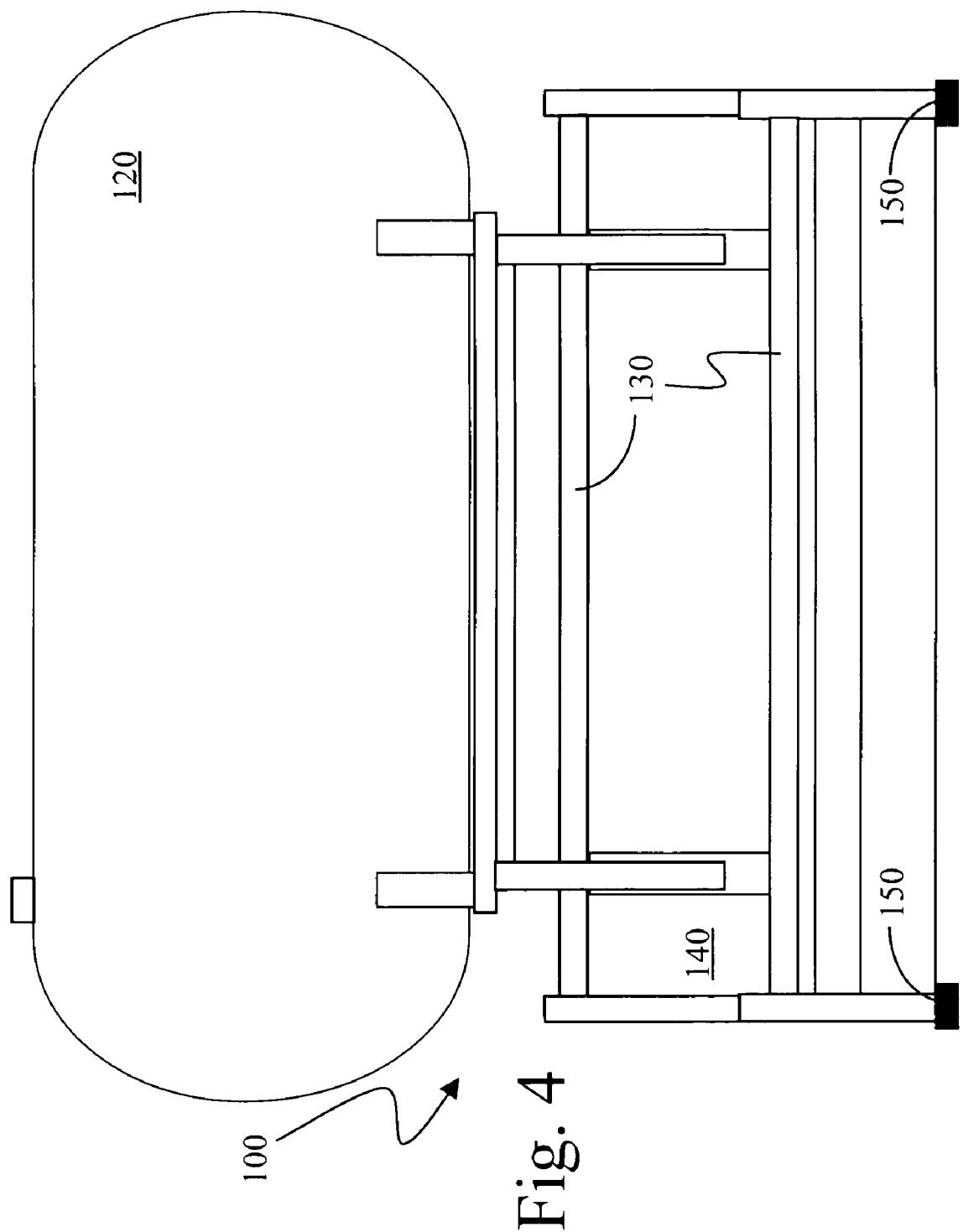
FIG. 4 is a rear elevation view of the tractor-drawn flamer.
Figure 8:
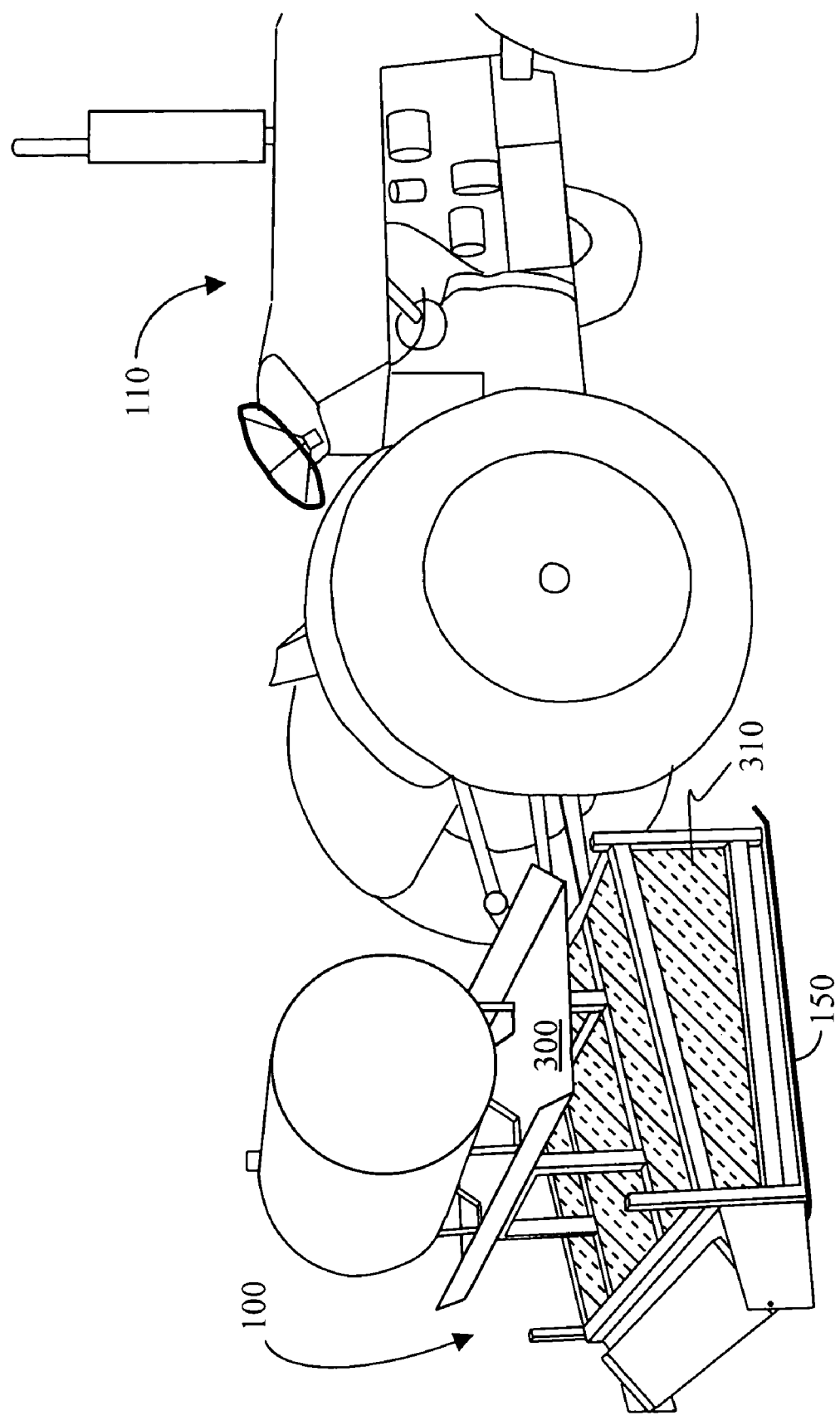
FIG. 8 is a perspective view of the tractor-mounted flamer showing a heat shield for the fuel tank and insulation around the skin of the flamer.

A perspective view of one embodiment of the present invention is shown in FIGS. 1, 2 and 8. A side view and a rear view are seen in FIGS. 3 and 4, respectively. A mobile flamer 100 is shown mounted on an implement hitch 105 of a tractor 110. Fuel may, optionally, be carried on the flamer in a fuel tank 120. A heat shield 300 for the fuel tank is shown in FIGS. 3 and 8, but is removed from FIGS. 1 and 4 for clarity. A suitable heat shield 300 comprises a sheet metal pan of adequate gage. In a second embodiment, the fuel may be separate from the flamer 100, for instance, carried on the tractor in a tractor-mounted fuel tank 220.

A hood for the flamer 100 comprises an external frame 130 and skin 140. Insulation 310 over the skin 140 is shown in FIGS. 3 and 8, and is an optional aspect for this invention. Because the frame is external to the skin 140, the frame is exposed to less radiant heat transfer, reducing the problems such as oxidation and fatigue caused by high temperatures and thermal cycling. In addition, the flamer 100 can be insulated while maintaining a reflective surface inside the flamer because frame 130 members are not in the way.

The skin 140 substantially contains the high temperature gases, protecting the surroundings and concentrating the heat to the material to be sterilized. Insulation 310 over the skin provides additional protection.

Adjustable skids 150 are used to maintain an appropriate height above the litter or other material 710 (see FIG. 7) to be sterilized. The weight of the flamer 100 may be shifted between the tractor hitch 105 and the skids 150, as needed. The flamer 100 is picked up with the tractor hitch 105 and carried off the surface for transport, cooling, etc.

Figure 5:
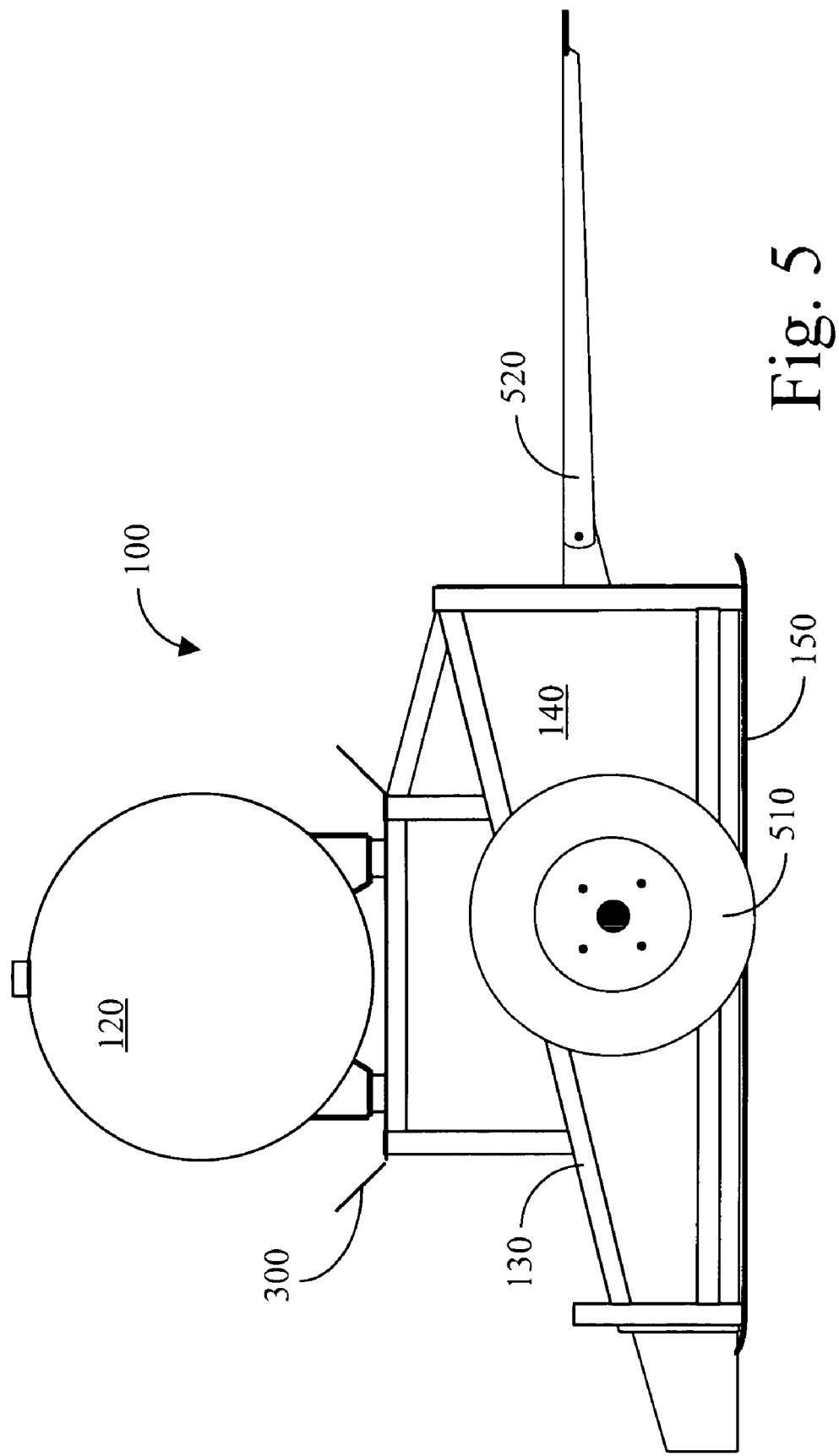
FIG. 5 is a side view of the wheel-mounted flamer.

An additional embodiment is shown in FIG. 5 wherein the flamer 100 is carried on wheels 510 and drawn behind the tractor 110 by its tongue 520. The wheels may be drawn up, allowing the flamer 100 to rest on its skids 150 when in use. One advantage to this embodiment is that the flamer 100 may be towed behind any of a multitude of vehicles such as a truck, four-wheeler, or tractor.

Figure 6:
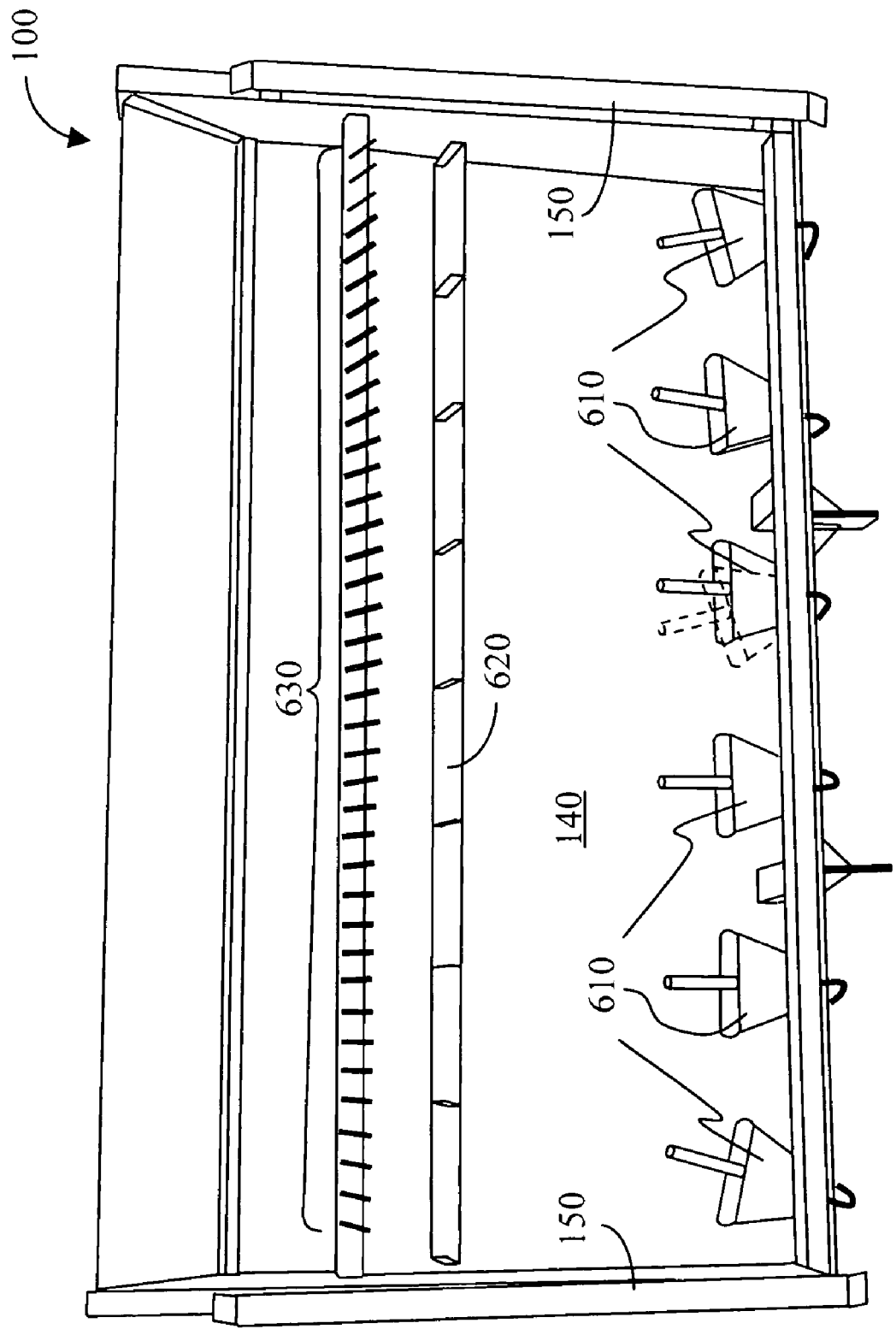
FIG. 6 is a perspective view of the underside of the tractor-mounted flamer.

The underside of the tractor-mounted flamer 100 is shown in FIG. 6. A front, or inlet, and a rear, or discharge, of the tractor-mounted flamer 100 are open to the ambient. A plurality of burners 610 are arrayed across the front of the flamer 100, the angles of which are adjustable, as shown by the dashed lines. In use, each of the plurality of burners 610 is oriented so that a flame emanating therefrom is directed in a substantially horizontal direction. A barrier 620 may optionally be provided to assist in concentrating the heat, containing the gases, and protecting the surroundings. An additional option is shown as a set of rake teeth 630 to loosen and stir the material 700 being sterilized.

Figure 7:
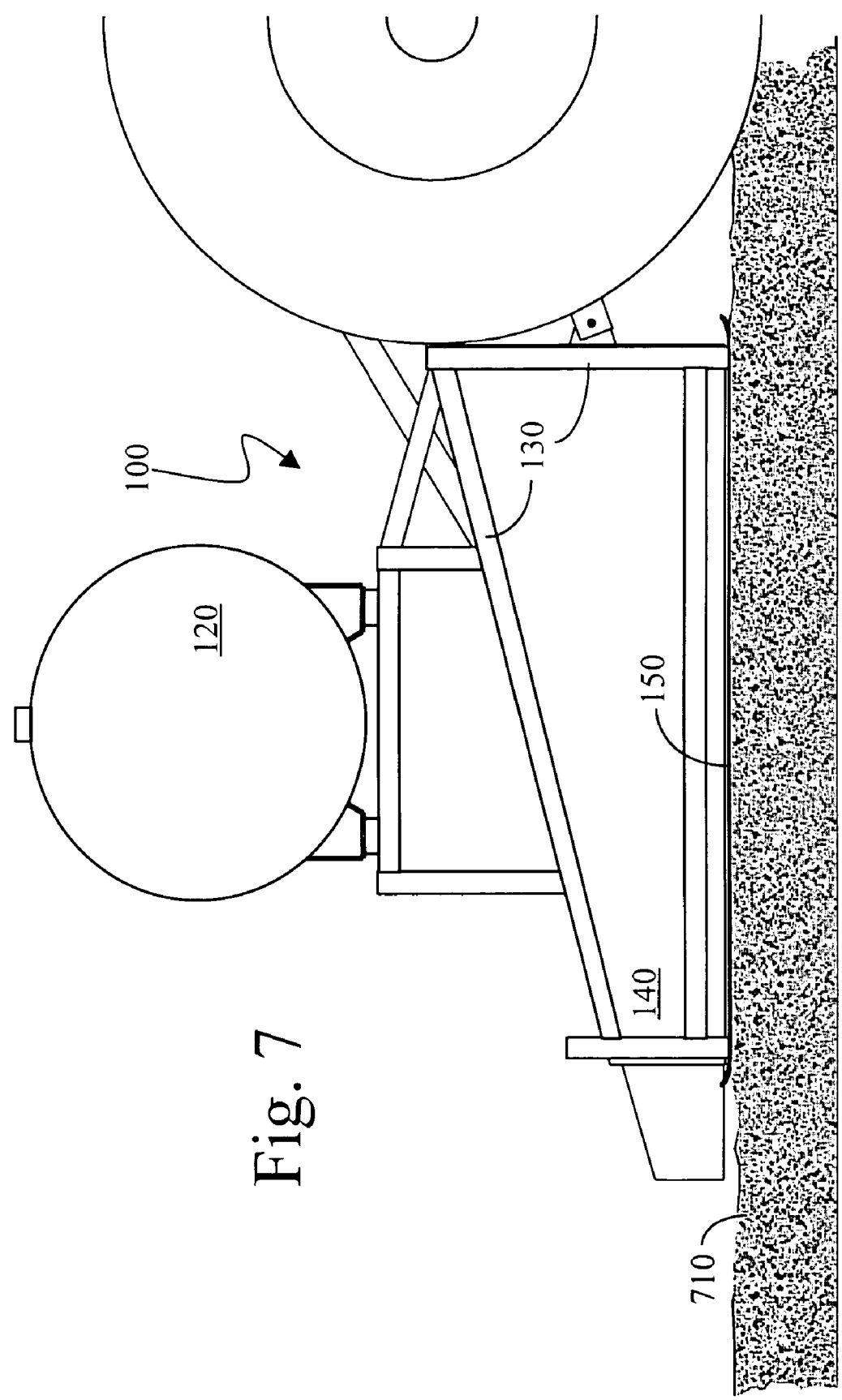
FIG. 7 is a side elevation view of the tractor-mounted flamer being used to sterilize a surface.

The flamer 100 of the present invention is shown in operation in FIG. 7. The surface material 710 being sterilized may be poultry litter, other livestock manure, soil, concrete, etc. The preferred method of sterilizing poultry litter using this invention includes the steps of holding poultry in confinement such that litter accumulates to form a surface; transporting a flamer to the litter surface; setting the flamer on skids on the surface; setting a flame to the burner such that the flame is contained within a hood; and heating the poultry litter sufficiently to kill microbes and bacteria.

The above embodiments are the preferred embodiments, but this invention is not limited thereto. It is, therefore, apparent that many modifications and variations of the present invention are possible in light of the above teachings. It is, therefore, to be understood that within the scope of the appended claims, the invention may be practiced otherwise than as specifically described.

I claim:

1. A method of sterilizing poultry litter, the method using an apparatus comprising a flamer having at least one burner situated under a hood, the hood being disposed completely over the top of a flame from the flamer; a hitch for attaching said flamer to a prime mover; the method of sterilizing poultry litter comprising:
   (a) holding poultry in confinement such that litter accumulates to form a surface;
   (b) transporting said apparatus to the litter surface;
   (c) setting a flame to the burner such that the flame is contained within and under the hood;
   (d) using the flame from the burner to heat the poultry litter surface sufficiently to kill microbes and bacteria; and
   (e) using a prime mover to move the flamer over the surface while heating the poultry litter.

2. The method of claim 1 wherein said using a prime mover to move the flamer over the surface is done by moving the apparatus along the surface on skids operatively attached to the hood while the skids are in contact with the surface.

3. An apparatus for sterilizing a surface, the apparatus having a forward direction corresponding to a towing vehicle forward direction, said apparatus comprising:
   (a) a hood for containing a flame;
   (b) an open inlet of the hood comprising a hood opening such that the hood is not sealed to the surface;
   (c) a plurality of burners situated under the hood;
   (d) a hitch for attaching said flamer to a tractor;
   (e) rake teeth disposed forward of the plurality of burners and under the hood; and
   (f) a baffler disposed between the rake teeth and the plurality of burners and under the hood.

* * * * *